United States Patent
Pannell et al.

(10) Patent No.: US 8,561,615 B2
(45) Date of Patent: *Oct. 22, 2013

(54) VASECTOMY DEVICES, KITS, AND METHODS OF USING SAME

(76) Inventors: William P. Pannell, Cordele, GA (US); Robert A. Van Wyk, Largo, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/540,873

(22) Filed: Jul. 3, 2012

(65) Prior Publication Data

US 2012/0266893 A1 Oct. 25, 2012

Related U.S. Application Data

(63) Continuation of application No. 11/934,871, filed on Nov. 5, 2007, now Pat. No. 8,220,464.

(60) Provisional application No. 60/856,304, filed on Nov. 3, 2006, provisional application No. 60/906,444, filed on Mar. 12, 2007.

(51) Int. Cl.
*A61F 6/02* (2006.01)
*A61B 17/00* (2006.01)
*A61B 18/18* (2006.01)

(52) U.S. Cl.
USPC .............. 128/842; 606/45; 606/51; 606/52

(58) Field of Classification Search
USPC .................. 606/21–52; 128/842, 898
See application file for complete search history.

(56) References Cited

U.S. PATENT DOCUMENTS

| | | |
|---|---|---|
| 3,762,417 A | 10/1973 | Textor |
| 4,803,983 A * | 2/1989 | Siegel .................. 606/151 |
| 4,920,982 A | 5/1990 | Goldstein |
| 5,026,379 A | 6/1991 | Yoon |
| 5,445,638 A | 8/1995 | Rydell et al. |
| 5,667,518 A | 9/1997 | Pannell |
| 5,702,390 A | 12/1997 | Austin et al. |
| 5,827,279 A * | 10/1998 | Hughett et al. .................. 606/45 |
| 5,891,141 A | 4/1999 | Rydell |
| 6,610,060 B2 | 8/2003 | Mulier et al. |
| 2001/0031961 A1 | 10/2001 | Hooven |
| 2002/0107517 A1 | 8/2002 | Witt et al. |
| 2002/0165531 A1 | 11/2002 | Goble |
| 2002/0169392 A1* | 11/2002 | Truckai et al. ................. 600/564 |
| 2002/0169446 A1 | 11/2002 | Mulier et al. |
| 2003/0069571 A1 | 4/2003 | Treat et al. |
| 2003/0078577 A1 | 4/2003 | Truckai et al. |
| 2003/0093068 A1 | 5/2003 | Hooven |
| 2004/0158286 A1 | 8/2004 | Roux et al. |
| 2004/0249368 A1 | 12/2004 | Hooven |
| 2005/0033284 A1* | 2/2005 | Hooven et al. .................. 606/41 |
| 2005/0101952 A1 | 5/2005 | Lands et al. |
| 2006/0069388 A1 | 3/2006 | Truckai et al. |
| 2008/0105265 A1 | 5/2008 | Pannell et al. |

* cited by examiner

*Primary Examiner* — Linda Dvorak
*Assistant Examiner* — Khadijeh Vahdat
(74) *Attorney, Agent, or Firm* — Chalin A. Smith; Smith Patent Consulting

(57) ABSTRACT

Conventional vasectomy techniques suffer from a number of disadvantages, including, for example, a substantial risk for the development of hematomas and swelling, a potential for spontaneous regeneration and undesired resumption of fertility, a need for a highly skilled surgical professional, as well as a long recovery period, accompanied by severe limitations on post-surgical activity. The invention disclosed herein overcomes the disadvantages and deficiencies of the prior art by providing a rapid, reliable, less invasive male sterilization procedure as well as a vasectomy device and kit for use therewith.

11 Claims, 22 Drawing Sheets

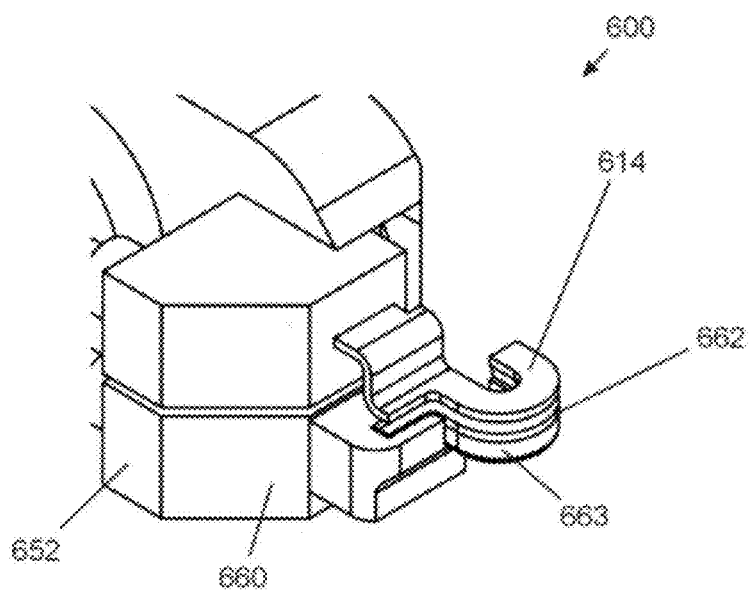
Fig. 33
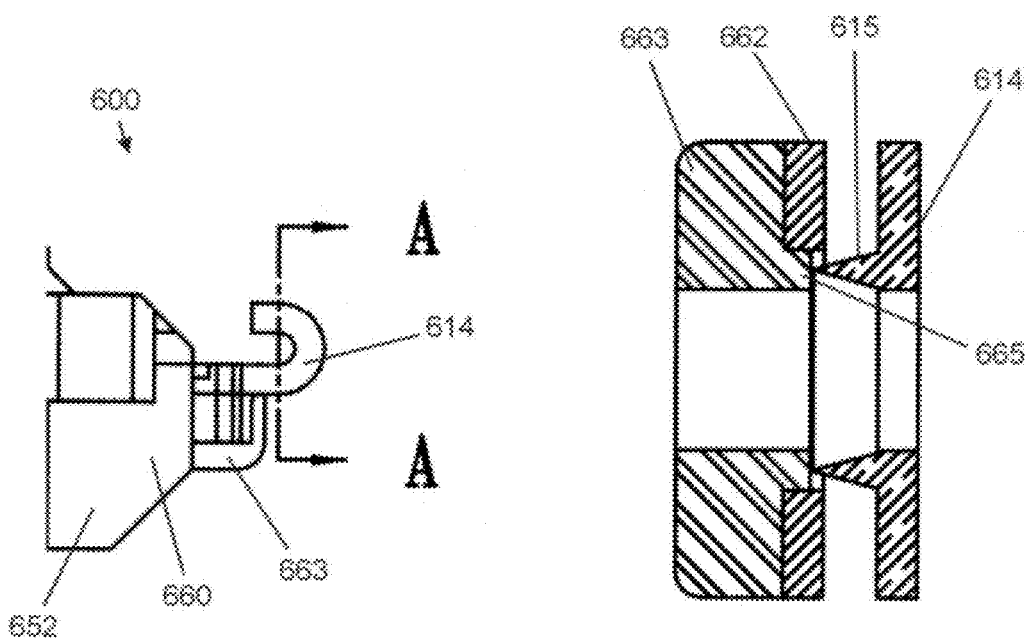
Fig. 34
Fig. 35

VASECTOMY DEVICES, KITS, AND METHODS OF USING SAME

PRIORITY

This application is a continuation of U.S. patent application Ser. No. 11/934,871 filed Nov. 5, 2007, now U.S. Pat. No. 8,220,464 issued Jul. 17, 2012, which, in turn, claims the benefit of U.S. Provisional Application Nos. 60/856,304 and 60/906,444, filed Nov. 3, 2006 and Mar. 12, 2007, respectively, the contents of which are hereby incorporated by reference in their entirety.

TECHNICAL FIELD OF THE INVENTION

The present invention relates to a surgical instrument, and more particularly to a surgical instrument and kit for performing vasectomies and a method for performing vasectomies using the instrument and kit.

BACKGROUND OF THE INVENTION

A vasectomy is surgical procedure which typically involves the removal of all or part of the ducts that carry sperm out of the testes (i.e., the vas deferens), thereby stopping the flow of sperm from the testicle to the prostate gland. After the vas deferens is interrupted, the sperm cannot be delivered and the man is rendered sterile. Unfortunately there are a few complications that are related to the procedure which cause significant concern but no real damage.

In non-elastic tissue, a small amount of bleeding is quickly stopped by the tension that develops in the tissue. However, the scrotal skin is highly elastic. Accordingly, a tamponade effect is created in most tissue that does not occur in the scrotum. Thus, even the slightest amount of persistent bleeding can cause tremendously large hematomas. Rough handling of the tissue, in a similar manner, causes significant swelling. Even the most experienced vasectomy surgeons occasionally encounter these problems.

Another problem associated with conventional vasectomy procedures involves the natural tendency of the cut ends of the vas deferens to grow back together, thereby allowing the flow of sperm to the prostate and resumption of fertility. Means for avoiding this failure has been the subject of debate among those skilled in the art, the question being whether the vas deferens should be clipped, cut, cauterized, ligated or all of the above. At present, the prevailing opinion for improving current procedures (discussed hereinafter) seems to be that further dissection (with the potential for further bleeding and swelling) should be used to remove a significant amount of tissue between the cut ends to minimize the possibility of contact.

Conventional vasectomy procedures are depicted in FIGS. 1 through 7 and discussed in detail hereinafter. As shown in the Figures, the vas deferens 2 is readily located within the scrotum 4, between testicles 6 and the prostate. As depicted in FIG. 1, a portion of the vas deferens 2 is trapped against the skin of the scrotum 4 by digital manipulation. As seen in FIG. 2, a standard blunt-tipped surgical clamp 8 (commonly referred to as a "vas clamp") is then used to temporarily hold the trapped duct 2 against the skin of the scrotum 4. The scrotum 4 is then punctured and the wound expanded sufficiently to allow dissection of the vas deferens 2, following which the duct 2 is grasped at partial thickness using a clamp 10 and extracted as shown in FIGS. 3 and 4. As seen in FIG. 5, the vas sheath 12 is retracted and an electrocautery with a blunt wire 14 is inserted into each hemitransected vas. In FIG. 6, ligation is complete. FIG. 7 depicts the anatomy after completion of the procedure on a vas deferens. For simplicity purposes, the above discussion describes only the principle steps, shown to demonstrate the principles of the procedure; intermediate steps have been eliminated. In any event, the large number of discrete steps creates multiple opportunities for complications. Also, the presence of bodily fluids during resection steps creates hazardous conditions for clinicians when performing the procedure on an HIV+ patient.

Thus, conventional vasectomy techniques suffer from a number of disadvantages, including, but not limited to, a substantial risk for the development of hematomas and swelling, a potential for spontaneous regeneration and undesired resumption of fertility, a need for a highly skilled surgical professional, as well as a long recovery period, accompanied by severe limitations on post-surgical activity. The present invention is intended to overcome disadvantages and deficiencies of the prior art.

SUMMARY OF THE PRESENT INVENTION

Thus, it is an object of the present invention to provide a rapid, reliable, less invasive male sterilization procedure as well as a novel vasectomy device and kit for use therewith. This and other objectives can be accomplished by the invention herein disclosed. However, regarding the specific objectives recited below, it will be understood by those skilled in the art that one or more aspects of this invention can meet certain objectives, while one or more other aspects can meet certain other objectives. Each objective may not apply equally, in all its respects, to every aspect of this invention. As such, the objects herein can be viewed in the alternative with respect to any one aspect of this invention.

It is an object of the present invention to provide a method for performing vasectomies that utilizes fewer steps than conventional vasectomy methods.

It is also an object of the present invention to provide a method for performing vasectomies which may be performed more quickly than current techniques. In some instances, both vas deferens may be treated in less than five minutes.

It is further an object of the present invention to provide a method for performing vasectomies that reduces the likelihood of complications, including for example, the onset of massive hematomas and swelling.

It is further an object of the present invention to provide a method for performing vasectomies which reduces or eliminates the possibility of spontaneous reconnection of the vas deferens, thereby eliminating an avenue for failure associated with conventional procedures.

It is further an object of the present invention to provide a method for performing vasectomies that allows patients to immediately resume normal activities, including, for example, showering and bathing.

It is further an object of the present invention to provide a method for performing vasectomies that allows patients to more quickly resume normal activities of daily living and work, providing a substantially shortened recovery period as compared with conventional vasectomies.

It is further an object of the present invention to provide a method for performing vasectomies in which there is little or no opportunity for contact with bodily fluids. In this manner, the method permits the performance on HIV+ patients and individuals with other blood-borne diseases (e.g., Hepatitis) with minimal risk to the clinician.

It is further an object of the present invention to provide a surgical instrument for performing vasectomies which allows the vasectomy procedure to be completed using a single instrument and a vas clamp.

It is further an object of the present invention to provide a surgical instrument for performing vasectomies which allows the vasectomy procedure to be performed by clinicians with limited training.

It is further an object of the present invention to provide a kit for performing vasectomies containing the novel surgical instruments of the present invention, coupled with other conventional materials that are required to complete the vasectomy procedure. Pursuant to the objectives listed herein, the present invention herein provides Pursuant to the objectives listed herein, the present invention herein provides a method for performing a vasectomy, optionally including the steps of: (a) locating the vas deferens within the scrotum; (b) temporarily isolating a length of the vas deferens in a fold of scrotal skin; (c) placing a clamping vasectomy device around a portion of the isolated scrotal skin containing the length of vas deferens, wherein the clamping vasectomy device is configured to retain an arcuate area of clamped scrotal tissue containing a first and second segment of the vas deferens, the clamping vasectomy device having an interior perimeter which defines a convex area of unclamped scrotal tissue that contains a third segment of the vas deferens; and (d) excising some or all of the convex area of unclamped scrotal tissue, including the third segment of vas deferens.

The clamping step may in one embodiment result in the physical crushing of the clamped scrotal tissue. In an alternate embodiment, the clamping step may result in the thermal coagulation of the clamped tissue. To that end, the present invention provides an alternate embodiment of the method for performing a vasectomy that includes the steps of: (a) locating the vas deferens within the scrotum; (b) temporarily isolating or trapping a length of the vas deferens in a fold of scrotal skin, for example by means of a standard vas clamp; (c) positioning an arcuate clamping vasectomy device around the portion of scrotal skin containing the isolated length of vas deferens, the clamping device being optionally connected to the bipolar output of an electrosurgical generator; (d) applying cauterizing energy, for example radio frequency (RF) power, to the clamped portion of scrotal tissue so as to thermally coagulate the tissue; and (e) excising or removing tissue the unclamped scrotal tissue defined by the curve of the clamping device, the excised tissue containing at least a portion of the vas deferens.

In either of the above-described embodiments, the step of locating the vas deferens may be accomplished through routine digital manipulation. Likewise, the step of temporarily isolating a length of the vas deferens may be accomplished using a standard vas clamp.

In either of the above-described embodiments, excision step may be achieved by means of conventional cutters (e.g., surgical scalpels and the like) or through electrosurgical ablation, using, for example a cutting electrode such as a bipolar RF electrode. The former embodiment necessitates a subsequent step of sealing the cut are, by means of surgical adhesive, suture, cauterization or a combination thereof.

The present invention further provides a vasectomy device for removing a section of the vas deferens trapped within a fold of scrotal skin, more particularly a clamping instrument having a proximal handle portion and a distal clamping portion, the clamping portion having a pair of opposingly faced upper and lower jaws movable between open and closed positions, wherein the jaws in the closed position are configured to retain an arcuate area of clamped tissue, wherein the jaws further include a pair of mating inner edges that engage to form a continuous curved perimeter which in use defines a convex area of unclamped tissue.

In one embodiment, the vasectomy device of the present invention may optionally further include a means for cauterizing clamped tissue, for example through inclusion of one or more electrodes having one or more output ends positioned on an engaging face of either or both of the upper and lower jaws.

In another embodiment, the vasectomy of the present invention may optionally further include a cutting electrode configured to slidably engage the continuous curved perimeter defined by the inner edges of the upper and lower jaws.

In yet another embodiment, the vasectomy of the present invention may optionally further include a power source, for example a radio frequency (RF) generator optionally mounted to the handle portion of the clamping instrument.

The present invention further provides a kit for performing a vasectomy containing the vasectomy device of the present invention in combination with one or more standard vas clamps. The kit may optionally further contain a local anesthetic and/or a power source, optionally mountable to the vasectomy device and/or composed of one or more rechargeable batteries capable of delivering cauterizing radio frequency energy.

These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF THE DRAWINGS

Various aspects and applications of the present invention will become apparent to the skilled artisan upon consideration of the brief description of the figures and the detailed description of the present invention and its preferred embodiments which follows:

FIG. 24 is an expanded view of the distal portion of the vasectomy device of

FIGS. 12 to 14 in use with coagulated tissue clamped between the jaws.

FIG. 33 is an expanded perspective view of the distal portion of an alternate embodiment formed in accordance with the principles of this invention.

FIG. 34 is a plan view of the objects of FIG. 33.

FIG. 35 is an expanded axial sectional view of the objects of FIG. 33 at location A-A of FIG. 34.

DETAILED DESCRIPTION OF THE PREFERRED EMBODIMENTS

Figure 1:
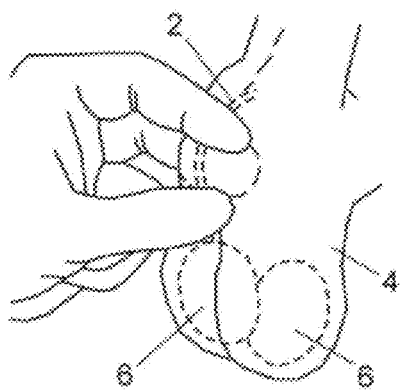
FIG. 1 is a prior art figure that depicts a perspective view of manual location of the vas deferens within the scrotum.

It is to be understood that this invention is not limited to the specific devices, systems, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims. It must be noted that as used herein and in the appended claims, the singular forms "a", "an", and "the" include plural reference unless the context clearly dictates otherwise. Thus, for example, reference to a "clamp" is a reference to one or more clamps and equivalents thereof known to those skilled in the art, and so forth.

All publications mentioned herein are incorporated herein by reference in their entirety. However, nothing herein should be construed as an admission that the invention is not entitled to antedate such disclosure by virtue of prior invention.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

As used herein, the noted directional terms relate to a human body in a standing position. For instance, "up" refers to in the direction of the head, "down" refers to in the direction of the feet. Herein, the "vertical" direction is parallel to the axis of the body and the "horizontal" direction is parallel to the floor. "Lateral" refers to the direction extending away from the center of the body whereas "medial" refers to a direction extending toward the center of the body.

In the context of the present invention, the term "proximal" refers to that end or portion of a device or instrument which is situated closest to the body of the subject when the device is in use.

In the context of the present invention, the term "distal" refers to that end or portion of a device or instrument which is situated farthest away from the body of the subject when the device is in use.

In the context of the present invention, the term "arcuate" is used herein to describe shapes forming or resembling an arch. It is used interchangeably with its synonym, arciform.

In the context of the present invention, the term "convex" refers to a surface or boundary that curves outward, as the exterior of a sphere. Conversely, the term "concave" refers to a surface or boundary that curves inward, as to the inner surface of a sphere, or is hollowed or rounded inward like the inside of a bowl. Herein, the area of unclamped scrotal tissue defined by the U-shaped jaws of the clamping vasectomy device of the instant invention and the arcuate area of clamped scrotal tissue contained therein is referred to as convex in shape.

As noted above, the present invention is characterized by substantial advantages not found in conventional methods and devices. For example, by avoiding direct dissection and resulting bleeding, the present invention is able to eliminate the risk for development of massive hematomas and swelling. In addition, the present invention allows for the separation of the vas deferens in such a manner that it is virtually impossible for the ends of the vas deferens to contact each other and rejoin. Also, the number of steps in the procedure is much less than for other current vasectomy techniques thereby reducing opportunities for complications. The inherent simplicity of the disclosed procedure and associated instruments simplifies training and allows clinicians with limited experience to master their use. Moreover, the procedures of the present invention avoid exposure to bodily fluids, which, in turn, minimizes risks of transmission of blood-born diseases, such a HIV and Hepatitis, to performing clinicians.

The present invention is further characterized by surgical instruments designed to perform vasectomies in accordance with the methods herein described. In one preferred embodiment, the instrument has clamping jaws, preferably a pair of opposingly faced upper and lower arcuate or "U" shaped jaws. The jaws may optionally be connected via electrical wiring to the bipolar output of an electrosurgical generator. The clamping jaws, when viewed in a plan view, preferably have a distal arcuate portion subjected to clamping pressure by the jaws, and an approximately semicircular center portion which is not subjected to clamping pressure. The jaws further include a lateral opening (or gap) that allows the clamping jaws to be positioned around a conventional vas clamp which serves to maintain the position of the vas deferens in the fold of scrotal skin. To prevent accidental shorting between the clamping jaws when connection with electrosurgical generator, the vas clamp is preferably formed from a suitable dielectric material, examples of which are readily known in the art.

In a particular preferred embodiment, the surgical instrument of the present invention is optionally provided with a movable cutting electrode on the distal end of a pivoting arm, such that when deployed the movable electrode intersects tissue within the semicircular center portion of the clamping jaws so as to electrosurgically remove the center portion. The cutting electrode is connected via circuitry within the instrument to the bipolar output of the electrosurgical generator. In a preferred embodiment, both the upper jaw and the cutting electrode are continuously connected to the same bipolar output cable of the generator. In an alternate embodiment, a switching means allows the first bipolar output of the generator to be connected to either the upper clamping jaw or the cutting electrode.

In use, a segment of the vas deferens is trapped within a fold of scrotal skin and its position is maintained using a standard vas clamp, optionally formed from a suitable dielectric material. The portion of the scrotum having the vas deferens is clamped between the jaws of the instrument, with the vas clamp in the center portion of the jaws. In one preferred embodiment, a ratchet mechanism may be included to maintain the clamping force. Energy can then be applied via the clamping jaws to the tissue trapped therebetween. In one embodiment, the energy may involve simple crushing of the captured tissue, which, in turn results in the formation of an arcuate area of crushed tissue. This tissue, because of the crush, will remain as a "cake" for a brief period of time, during which the tissue held by standard vas clamp.

In an alternate embodiment, the energy may take the form of thermal energy, preferably in the form of RF power from the electrosurgical generator, the power level being sufficient to thermally coagulate the tissue thereby sealing the ends of the vas deferens, fusing them to the scrotal skin, and fusing the fold in the scrotal skin so as to form a contiguous mass. The length of time for coagulation is determined by the operator, typically through foot pedal activation of the generator. In a preferred embodiment, the electrosurgical unit monitors the impedance of the tissue between the clamped jaws of the instrument and based on changes in the impedance determines when coagulation is complete. In another embodiment, the time duration during which power is supplied to the instrument for coagulation is determined by a timer within the electrosurgical unit. When the tissue is fully coagulated, while the tissue is still clamped between the jaws, the vas clamp is removed. Subsequently, the electrosurgical unit is activated so as to allow the cutting electrode to remove the un-coagulated tissue in the center of the coagulated arcuate portion, after which the cutting electrode returns to its original position. The ratchet can then be released, which, in turn, allows the clamping jaws to be removed from the site. In this embodiment, closure of the wound by suturing or adhesive is not required. Accordingly, the patient may bathe or shower as soon as desired. Although traditional vasectomies recommend minimal activity for 48 hours and limited activities for one week, in the context of the present invention there are no contra-indications to the patient resuming any normal activity that does not involve direct trauma to the scrotum.

The surgical instrument herein described has components that are preferably formed from injection moldable polymeric materials having molded therein, when required, metallic components that permit connection to electrical circuitry at their proximal end, and either a clamping jaw or a cutting electrode at their distal end. In a preferred embodiment, the instrument takes the form of a single-use disposable product, while in another embodiment, it is constructed for limited reuse.

The present invention is further characterized by a kit for performing vasectomies, the kit containing the clamping/resecting surgical instrument of the present invention in combination with one or more standard vas clamps, preferably formed from a suitable dielectric material.

Although any methods and materials similar or equivalent to those described herein can be used in the practice or testing of embodiments of the present invention, particular aspects and preferred embodiment of the present invention are depicted in the accompanying figures and described hereinafter. However, the embodiments described herein are merely intended to illustrate the principles of the invention. Those skilled in the art will recognize that variations and modifications may be made to the embodiments without changing the principles of the invention herein disclosed. Accordingly, the accompanying figures, described in detail below, that depict aspects of the invention are in no way intended to limit the scope of the present invention.

Figure 8:
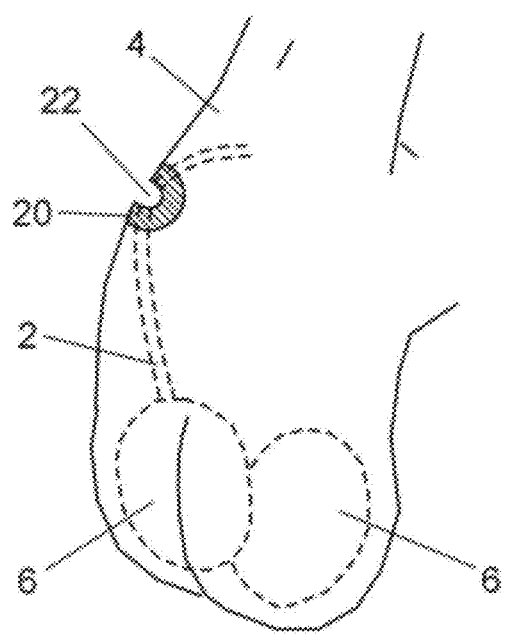
FIG. 8 depicts a portion of the anatomy after a vasectomy operation in accordance with the principles of this invention.

Referring now to FIG. 8, portion of the anatomy after completion of a vasectomy performed in accordance with the principles of this invention is depicted. Arcuate portion 20 containing first and second segments of the vas deferens 2 and skin of scrotum 4 has been coagulated so as to form a contiguous structure, and center portion 22 of which, containing a third segment of the vas deferens 2 and scrotal skin 4, has been removed.

Figure 9:
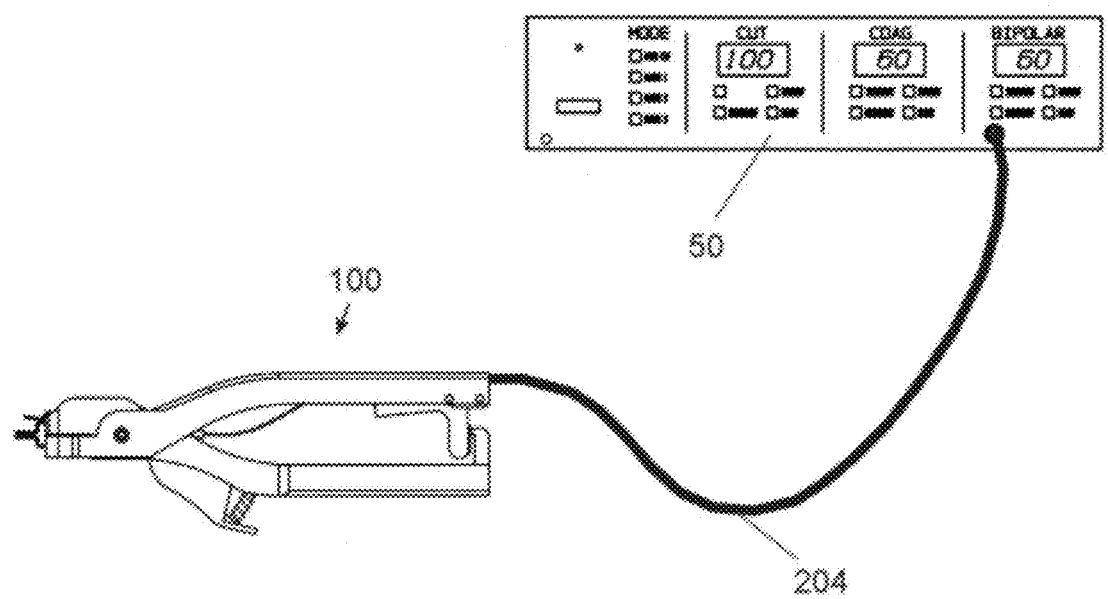
FIG. 9 depicts a system for performing vasectomies including an instrument constructed in accordance with the principles of this invention.
Figure 10A:
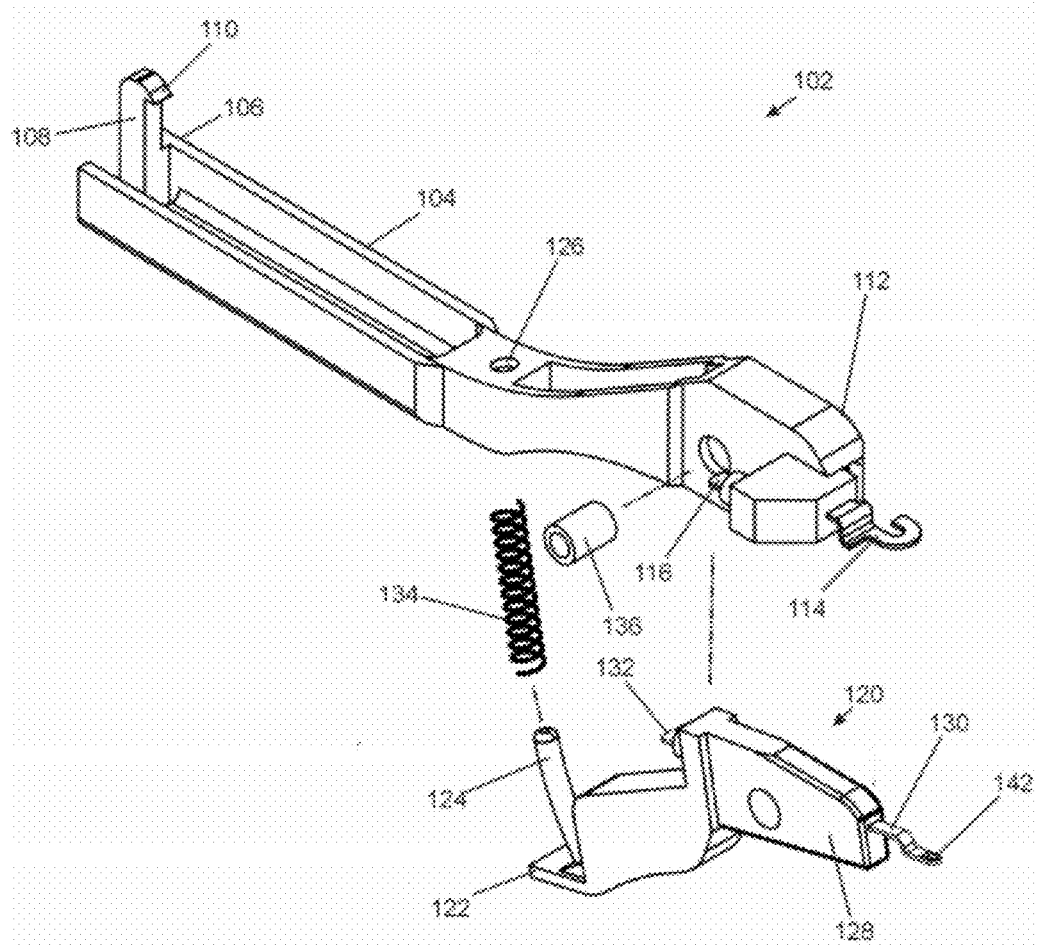
FIG. 10(a) is an exploded view of a first subassembly of a vasectomy device constructed in accordance with the principles of this invention.
Figure 10B:
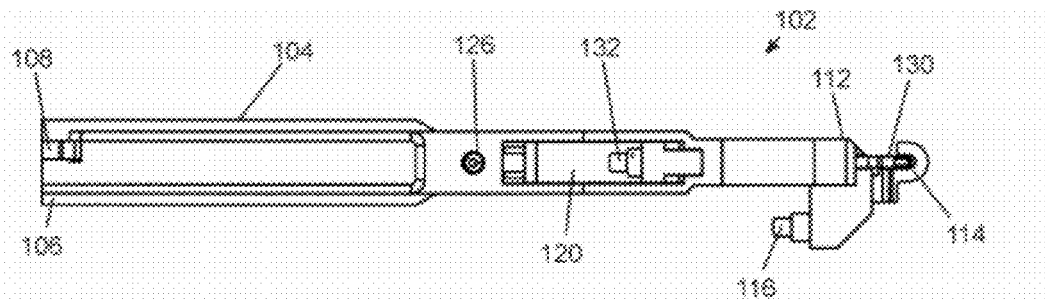
FIG. 10(b) is a plan view of the objects of FIG. 10(a).
Figure 10C:
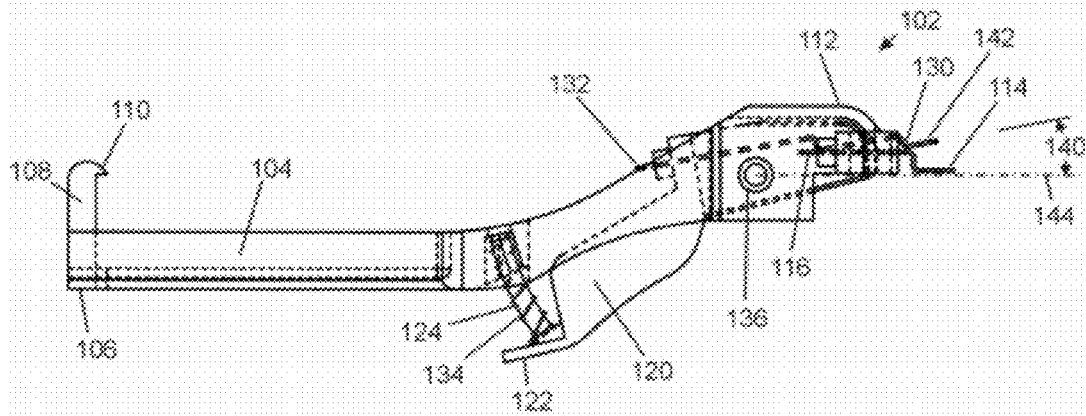
FIG. 10(c) is a side elevational view of the objects of FIG. 10(a)
Figure 10D:
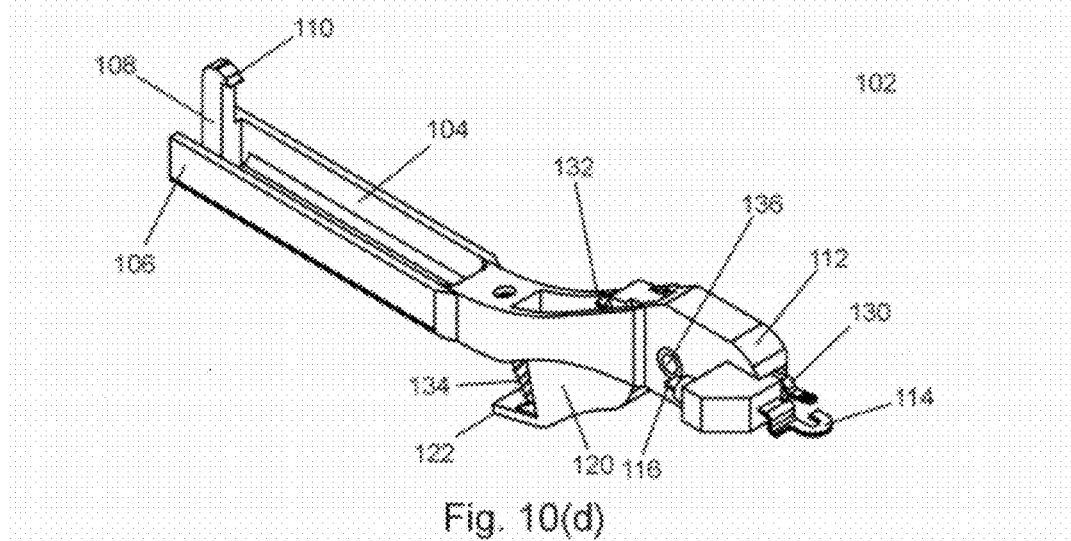
FIG. 10(d) is a perspective view of the objects of FIG. 10(a).
Figure 11A:
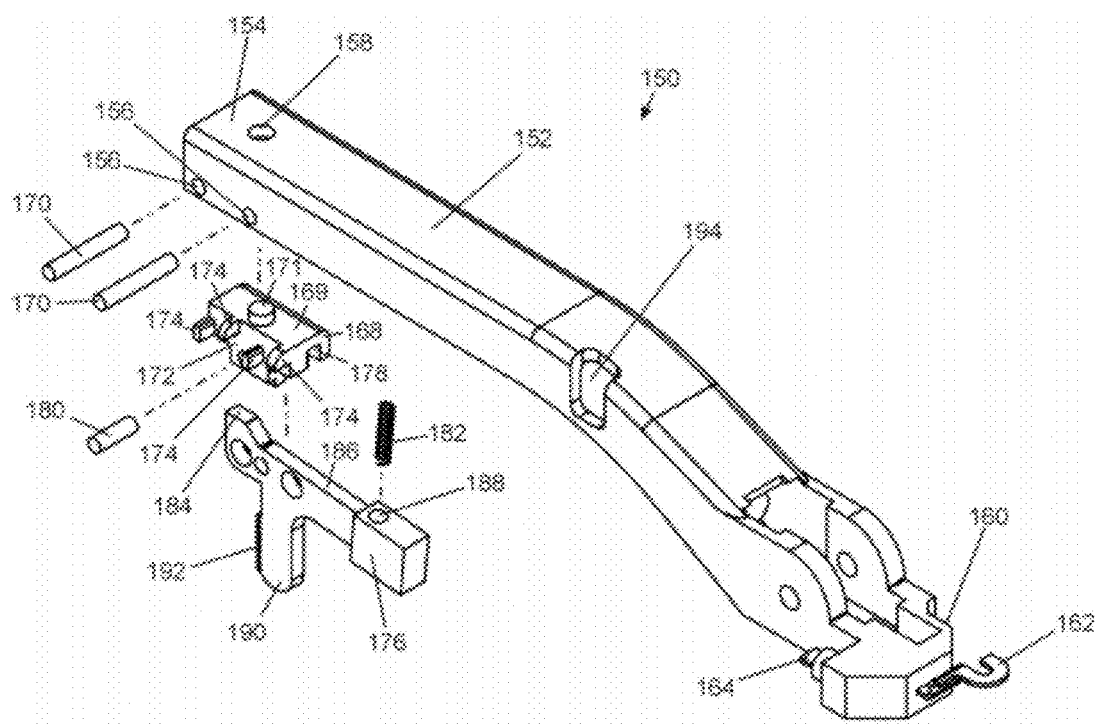
FIG. 11(a) is an exploded view of a second subassembly of a vasectomy device constructed in accordance with the principles of this invention.
Figure 11B:
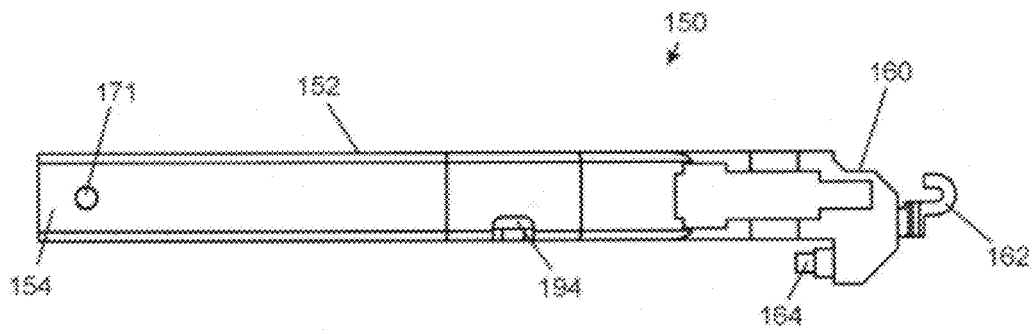
FIG. 11(b) is a plan view of the objects of FIG. 11(a).
Figure 11C:
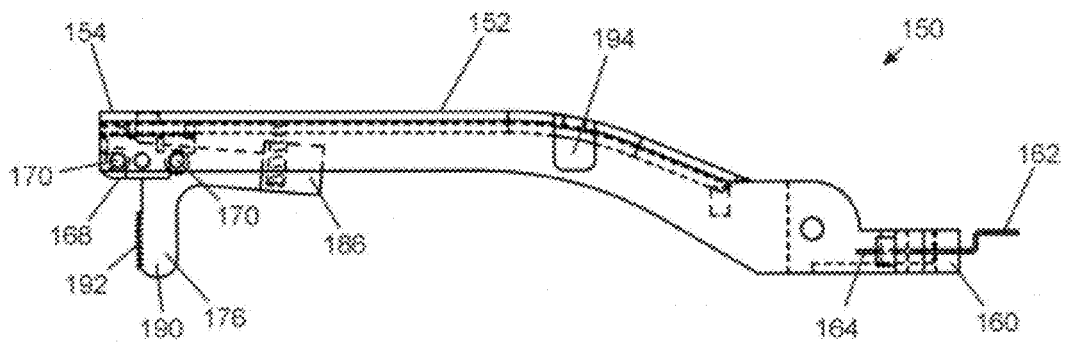
FIG. 11(c) is a side elevational view of the objects of FIG. 11(a).
Figure 11D:
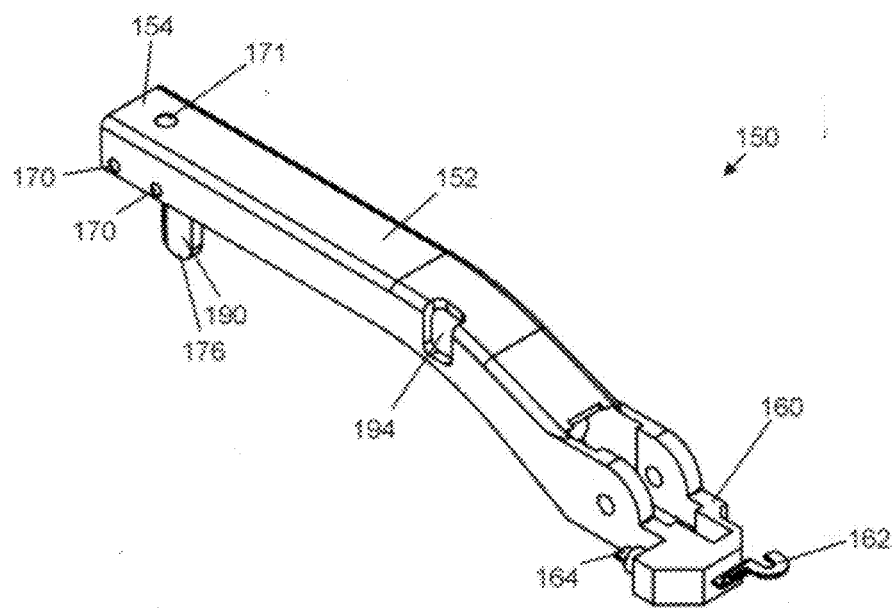
FIG. 11(d) is a perspective view of the objects of FIG. 11(a).

FIG. 9 depicts an illustrative vasectomy device 100 constructed in accordance with the principles of the present invention connected by electrical cable 142 to electrosurgical generator 50.

FIGS. 10(a) through 10(d) depicts a first subassembly 102 of device 100. Subassembly 102 has a first member 104 with a proximal end 106 having a vertical portion 108 the top of which has a tapered distal facing portion 110. Member 104 has a distal end 112 having an upper clamping jaw 114 electrically connected to connector portion 116. In a preferred embodiment member 104 is injection molded form a suitable polymeric material, and jaw 114 and connector portion 116 are portions of a stamping formed from stainless steel, titanium, nickel, or another suitable conductive or metallic material, the stamping being inserted into the injection mold prior to injection of the polymeric material. Second member 120 has a proximal end 122 having a more or less vertical arcuate protuberance 124 having a diameter less than that of hole 126 in the mid-portion of first member 104, and less than the internal diameter of spring 134 such that on assembly protuberance 124 is positioned within spring 134. Distal end 128 of second member 120 has protruding distally therefrom electrode 130 which is electrically connected to connector portion 132. In a preferred embodiment, the second member 120 is injection molded form a suitable polymeric material, and electrode 130 and connector portion 132 are portions of a stamping formed from stainless steel, titanium, nickel, or another suitable conductive or metallic material, the stamping being inserted into the injection mold prior to injection of the polymeric material. Second member 120 is pivotably positioned within first member 104 by sleeve 136, spring 134 causing second member 120 to be rotated such that distal end 142 of electrode 130 is displaced angle 140 from line 144.

FIGS. 11(a) through 11(d) depict a second subassembly 150 of device 100. Member 152 has a proximal end 154 with mounting holes 156 and locating hole 158, and a distal end 160 from which protrudes lower clamping jaw 162 which is electrically connected to connector portion 164. In a preferred embodiment, member 152 is injection molded form a suitable polymeric material, and lower clamping jaw 162 and connector portion 164 are portions of a stamping formed from stainless steel, titanium, nickel, or another suitable conductive or metallic material, the stamping being inserted into the injection mold prior to injection of the polymeric material. Mounting block 168 is mounted to proximal end 154 of member 152 by pins 170. Lateral surface 172 of block 168 has a plurality of protuberances 174 which form a labyrinth strain relief for an electrical cable placed therein. Upper surface 169 of block 168 has formed thereon cylindrical protrusion 171 which engages locating hole 158 in member 152 when block 168 is mounted to member 150. Ratchet arm 176 is pivotably mounted in channel 178 of block 168 by pin 180, spring 182 causing arm 176 to rotate such that proximal stop portion 184 of arm 176 contacts the upper surface of channel 178. First portion 186 of arm 176 has formed therein spring pocket 188 for containing spring 182. Second portion 190 of arm 176 has formed in its proximal surface ratchet teeth 192. Member 152 has formed therein opening 194.

Figure 12:
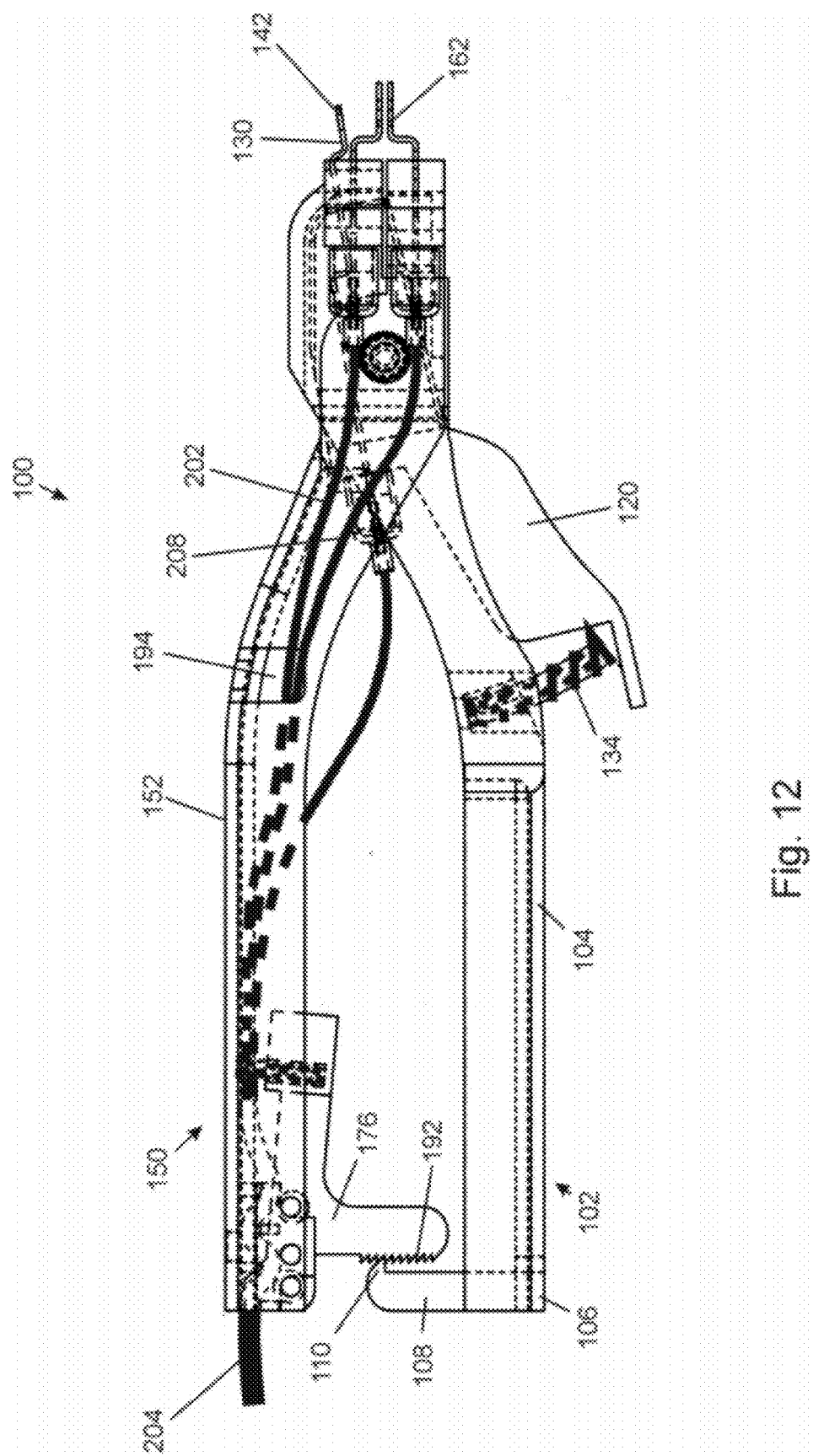
FIG. 12 is a side elevational view of a vasectomy instrument constructed in accordance with the principles of this invention.

Referring now to FIG. 12 depicting device 100, subassembly 102 is pivotably assembled to subassembly 150 by pin 200 passing through holes 196 in member 152 and sleeve 136 of subassembly 102 such that member 120 pivots freely within member 104, and member 104 of subassembly 102 pivots freely within member 152. Teeth 192 of ratchet arm 176 in cooperation with tapered distal portion 110 of vertical portion 108 of member 102 maintain clamping pressure between lower jaw 162 and upper jaw 114. Electrical cable 202 connects connector portion 116 connected to upper jaw 114 to cable 204. Electrical cable 208 connects connector portion 164 connected to lower jaw 162 to cable 204. Cable 212 connects connector portion 132 connected to electrode 130 to cable 204. Cables 202, 208 and 212 have at their distal terminal ends mating connector portions which together with portions 116, 164 and 132 form connector pairs, the connector pairs forming sealed assemblies.

Figure 13:
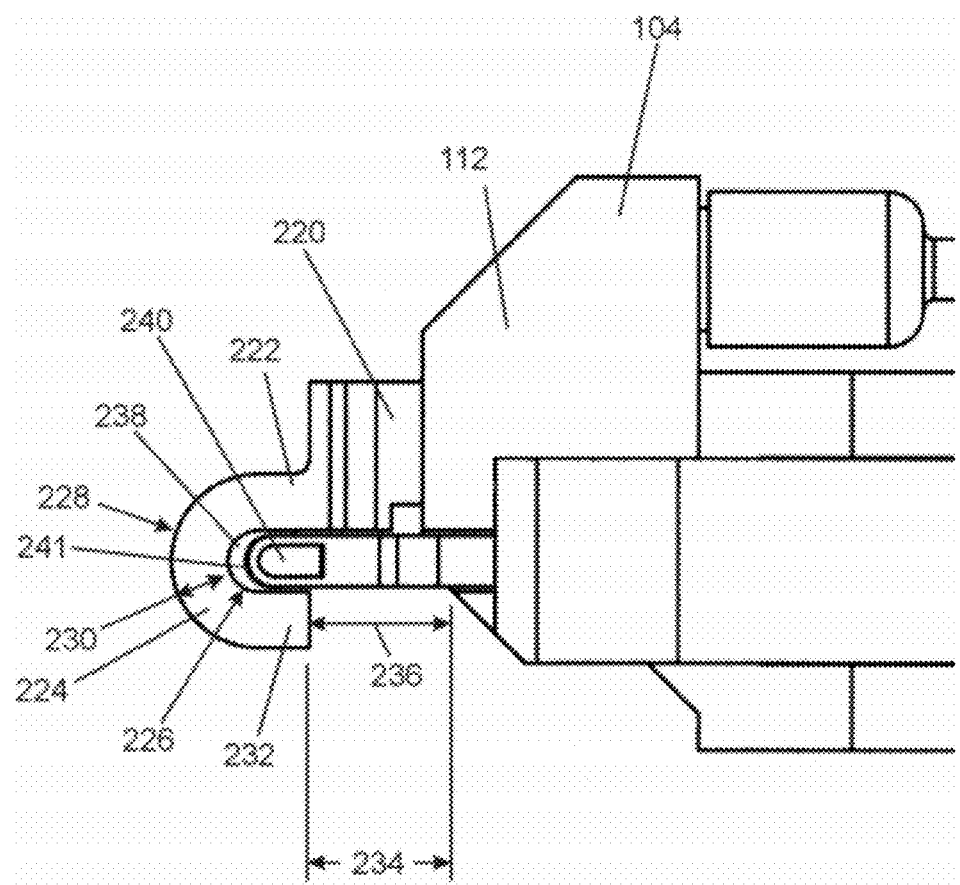
FIG. 13 is an expanded plan view of the distal portion of the objects of FIG. 12.

When viewed in a plan view as in FIG. 13, jaws 114 and 162 (hidden beneath jaw 114) each have a proximal portion 220 connecting ends 222 of arcuate distal portions 224 to members 104 and 152, arcuate distal portions 224 having an inner radius 226, an outer radius 228, and a radial width 230. Ends 232 of arcuate portions 224 are displaced distally from members 104 and 152 distance 234 so as to form a gap 236. Inner radius 226 is preferably between 0.5 and 4 millimeters, and more preferably between 1 and 3 millimeters. Radial width 230 is preferably between 1 and 6 millimeters, and more preferably between 2 and 4 millimeters. Arcuate distal portions 224 define inner regions 238. Electrode 130 has formed in its distal portion 150 opening 240 so as to form a perimitral ring 241.

Figure 14:
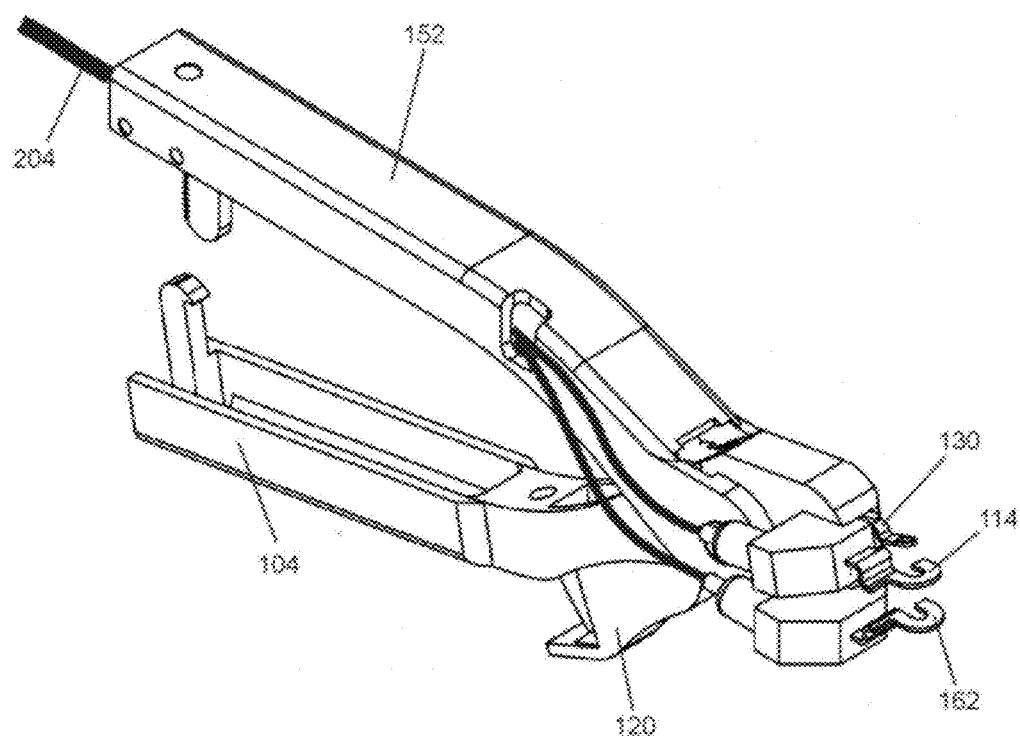
FIG. 14 is a perspective view of the device of FIG. 12 with the clamping jaws opened for use.

FIG. 14 depicts device 100 ready for use in performing a vasectomy, jaws 114 and 162 being angularly displaced so as to allow the placement of tissue therebetween for clamping.

Figure 15:
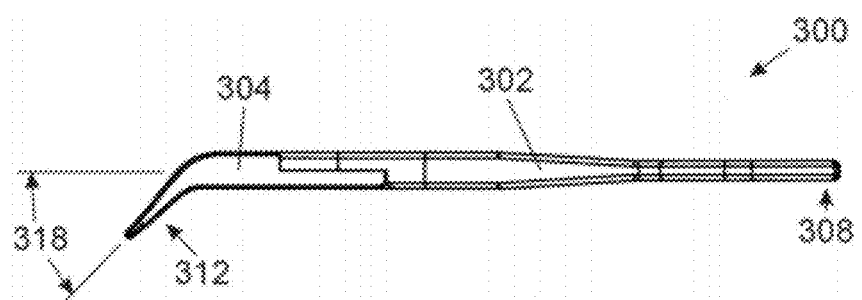
FIG. 15 is a plan view of a clamping instrument formed in accordance with the principles of this invention and suitable for use with the vasectomy device of FIG. 12.
Figure 16:
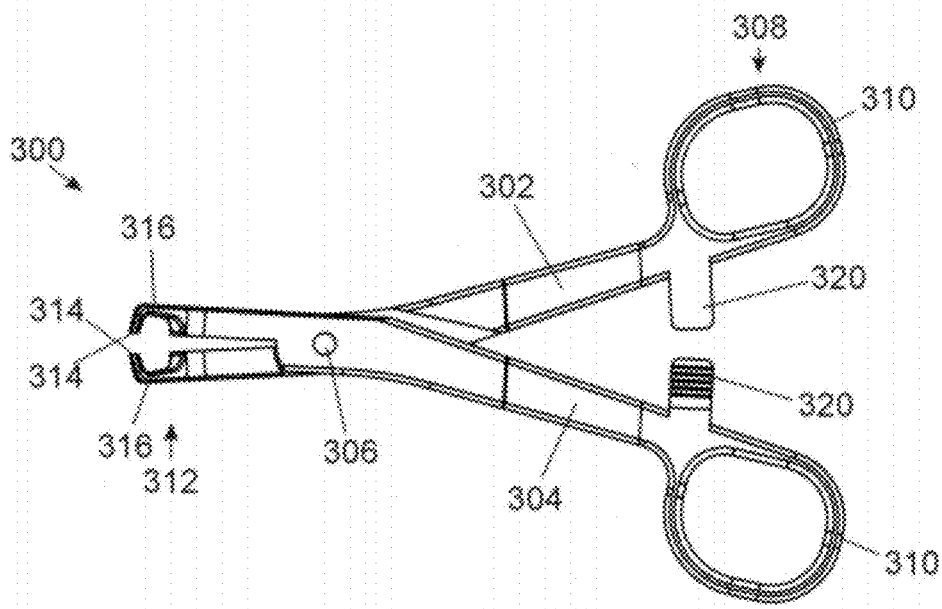
FIG. 16 is a side elevational view of the objects of FIG. 15.
Figure 17:
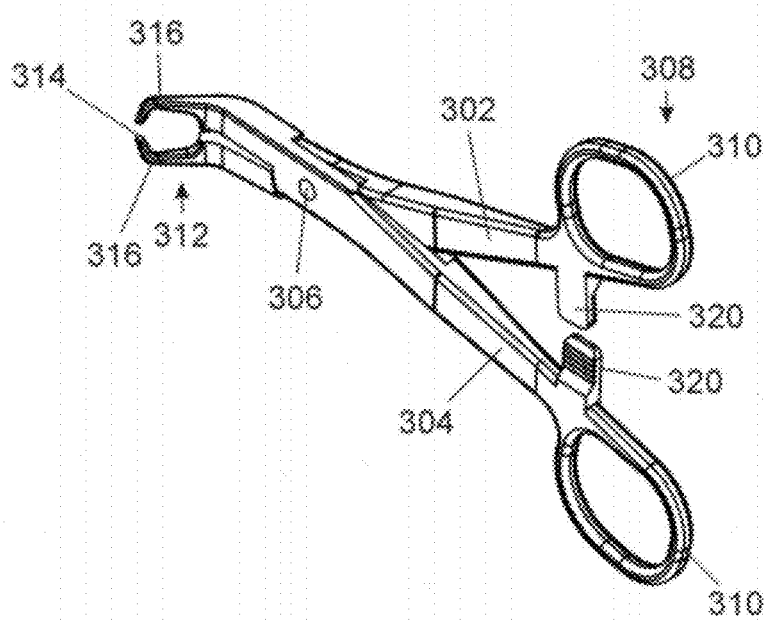
FIG. 17 is a perspective view of the objects of FIG. 15.

Performing a vasectomy according to the method in accordance with the principles of this invention requires the use of vasectomy device 100, and a clamping instrument 300, depicted in FIGS. 15 through 17, formed from a suitable dielectric material. In a preferred embodiment instrument 300 is formed from a thermoplastic material by injection molding. In a further preferred embodiment, the injection moldable thermoplastic is a composite material having an inorganic filler material for added rigidity. Clamping instrument 300 has a first member 302 and a second member 304, members 302 and 304 together forming a clamping assembly rotatably joined by pivot 306, the assembly having a proximal end 308 forming finger loops 310, and a distal end 312 forming clamping surfaces 314 having adjacent thereto arched portions 316. When viewed in a plan view as in FIG. 16, distal end 312 is offset from the body of instrument 300 angle 318. Interlocking portions 320 maintain clamping force on tissue between clamping surfaces 314, sideways pressure on proximal ends 308 releasing the clamping force.

Figure 2:
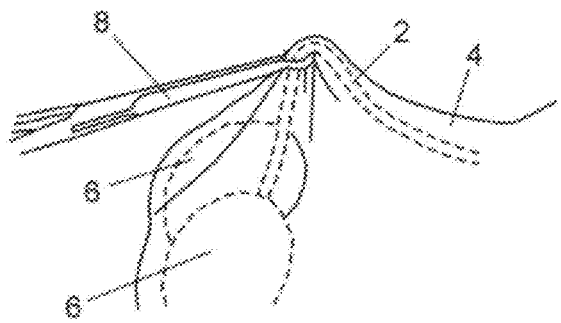
FIG. 2 is a prior art figure that depicts a perspective view of the vas isolated in a fold of the scrotum using a vas clamp.
Figure 3:
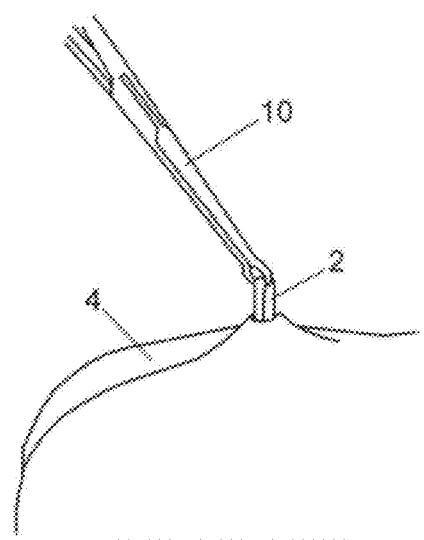
FIG. 3 is a prior art figure that depicts a step in a conventional vasectomy procedure in which the vas deferens is extracted from the scrotum
Figure 4:
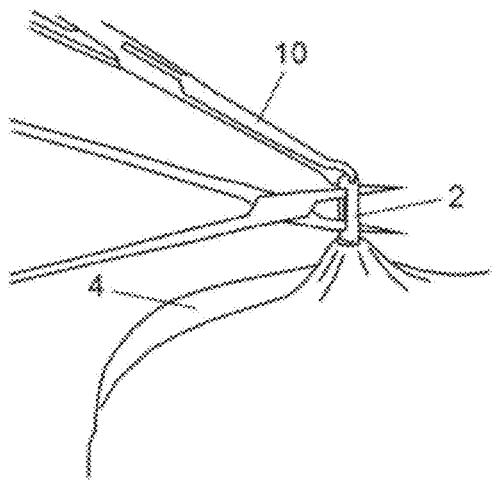
FIG. 4 is a prior art figure that depicts a step in a conventional vasectomy procedure in which the vas deferens is dissected.
Figure 5:
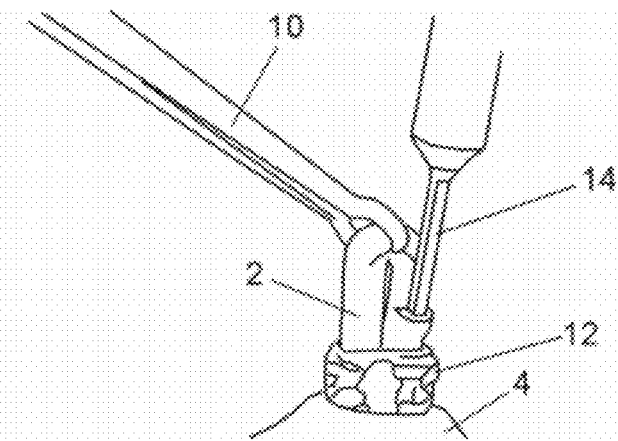
FIG. 5 is a prior art figure that depicts a step in a conventional vasectomy procedure in which the sheath has been retracted on the vas duct and electrocautery is used to FIG. 6 is a prior art figure that depicts a step in a conventional vasectomy procedure in which ligation is complete.
Figure 6:
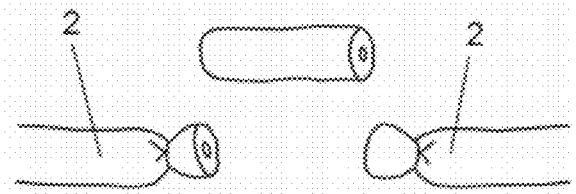
Figure 7:
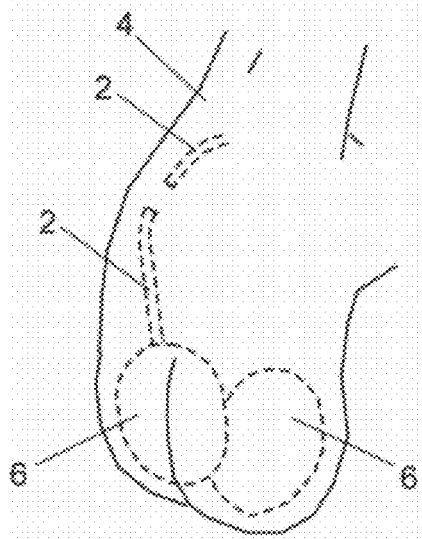
FIG. 7 is a prior art figure that depicts the anatomy at the completion of a conventional vasectomy procedure.
Figure 18:
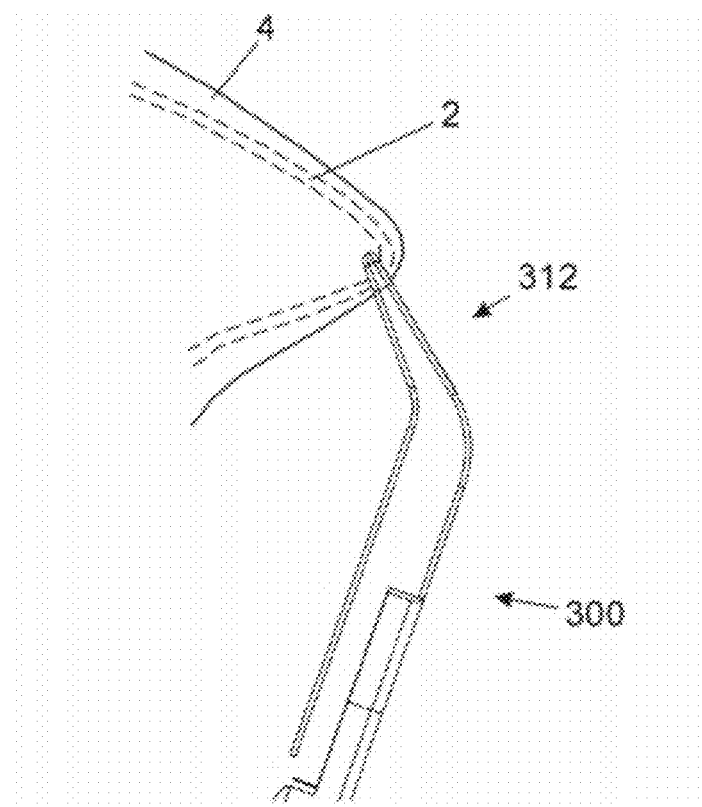
FIG. 18 is a plan view of the clamping instrument of FIG. 15 suitable for use in a vasectomy procedure.
Figure 19:
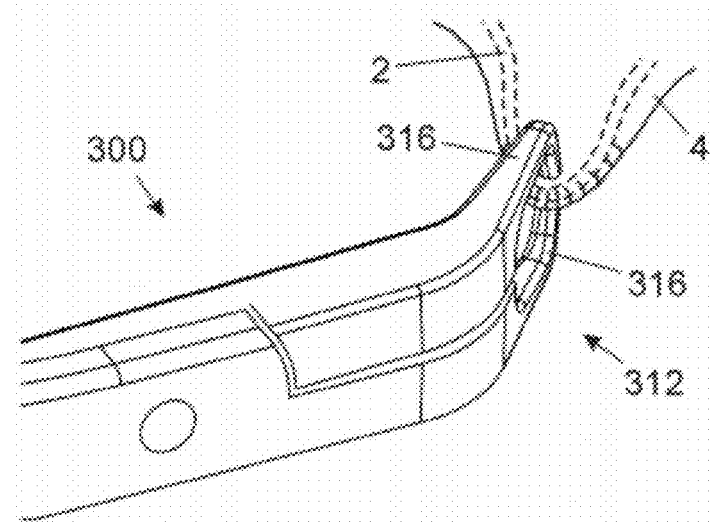
FIG. 19 is a perspective view of the objects of FIG. 18.
Figure 20:
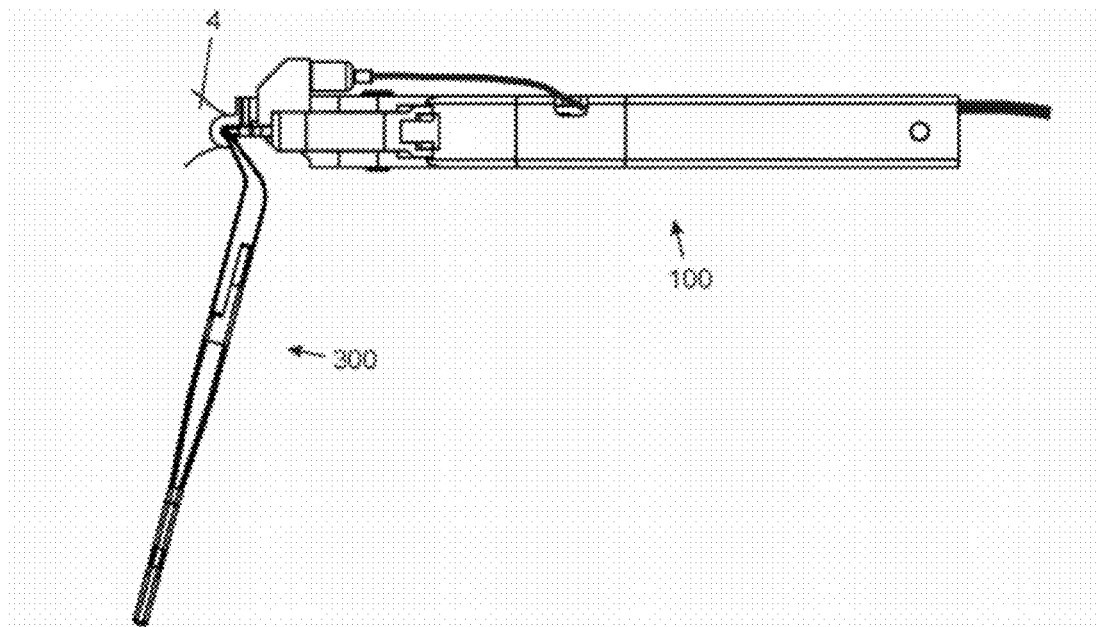
FIG. 20 is a plan view of the clamping instrument of FIG. 15 suitable for use with the vasectomy device of FIGS. 12 to 14.
Figure 21:
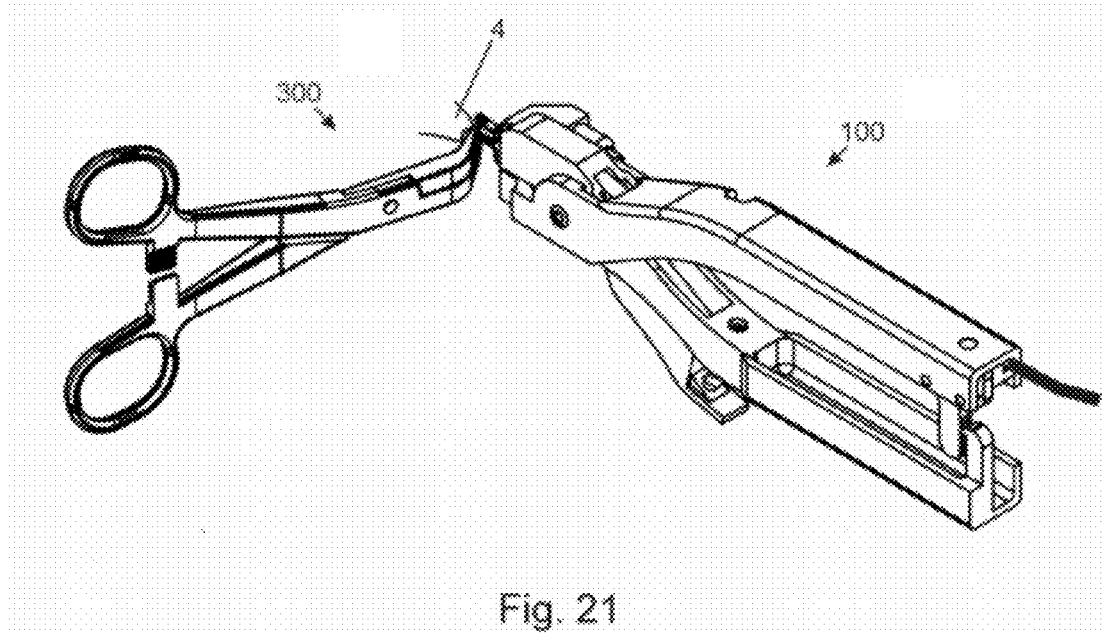
FIG. 21 is a perspective view of the objects of FIG. 20.
Figure 22:
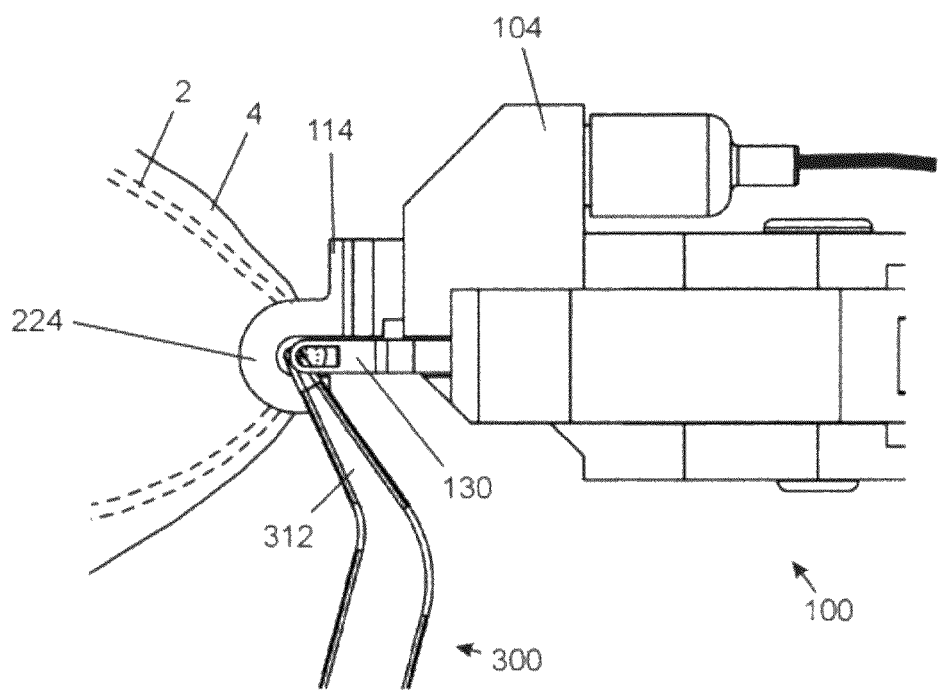
FIG. 22 is an expanded plan view of the distal portion of the objects of FIG. 20.
Figure 23:
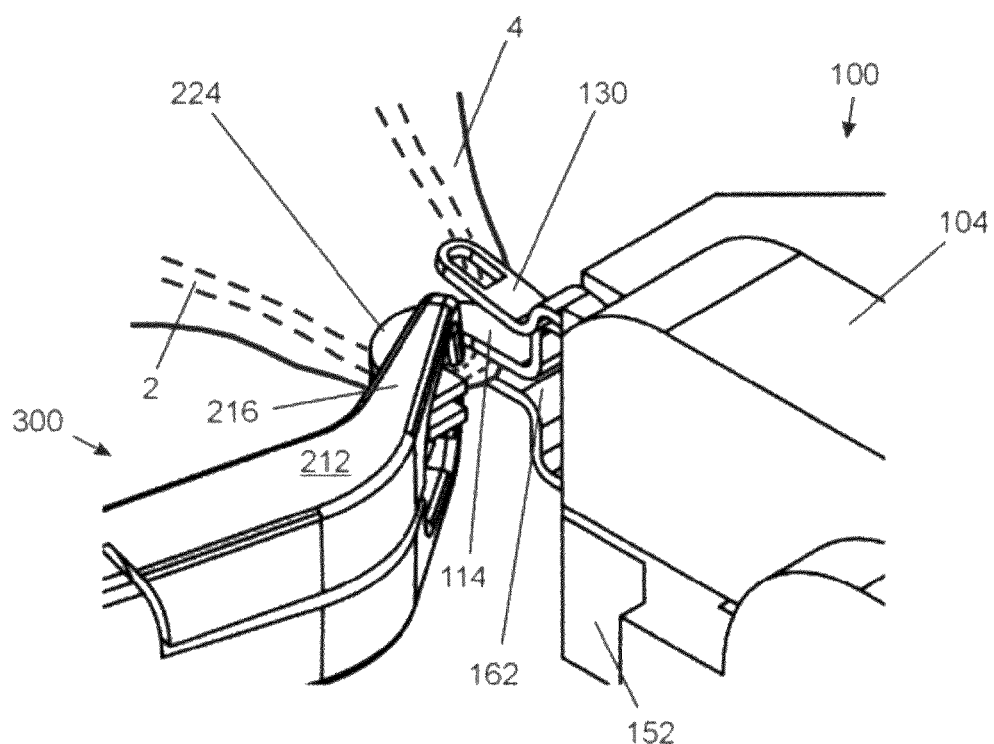
FIG. 23 is an expanded perspective view of the objects of FIG. 22.
Figure 24:
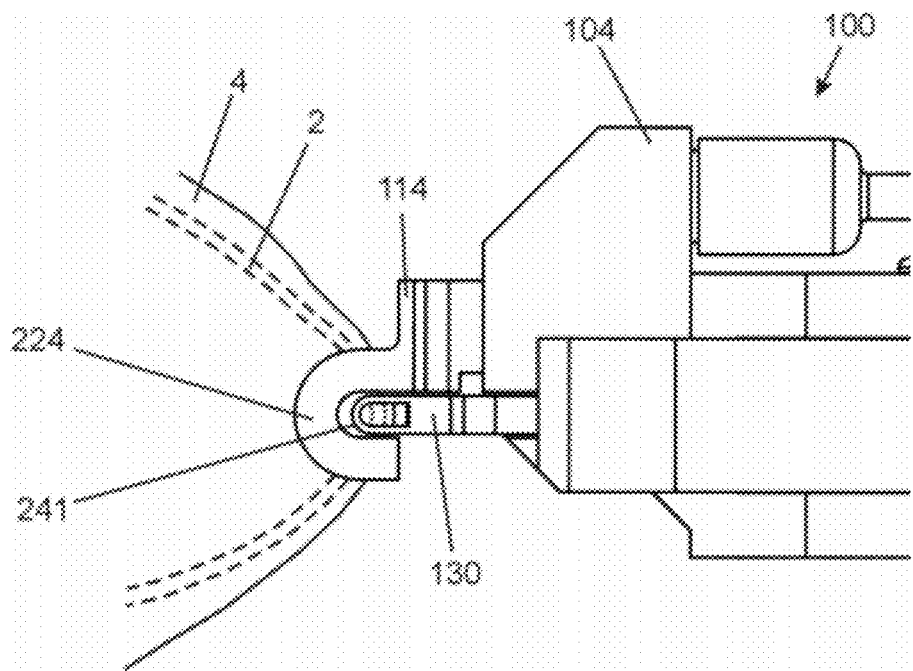
Figure 25:
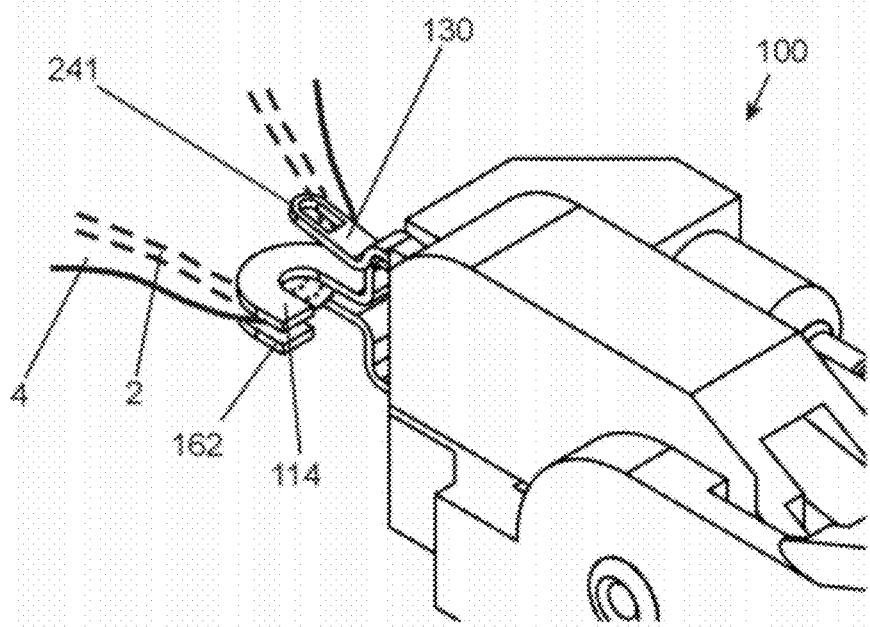
FIG. 25 is a perspective view of the objects of FIG. 24.
Figure 26:
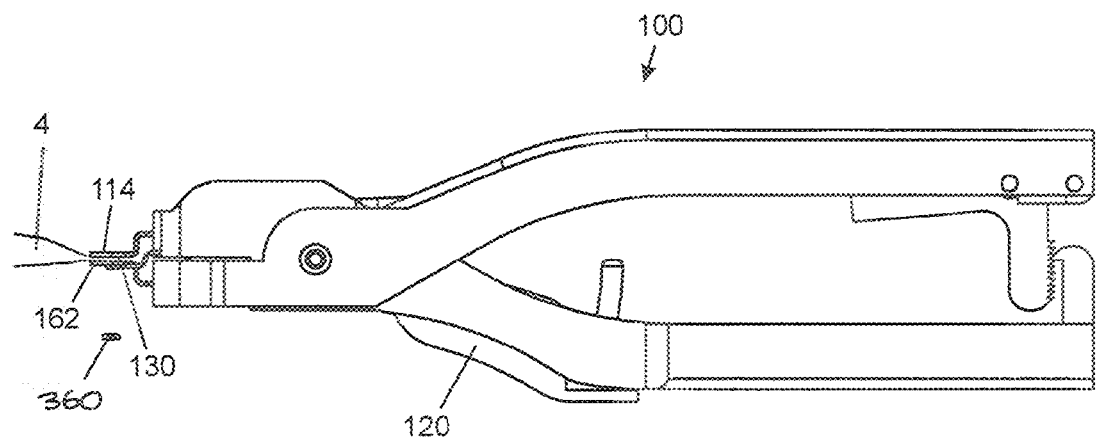
FIG. 26 is a side elevational view of the vasectomy device of FIGS. 12 to 14 at the completion of a vasectomy procedure before the clamping jaw pressure is released.
Figure 27:
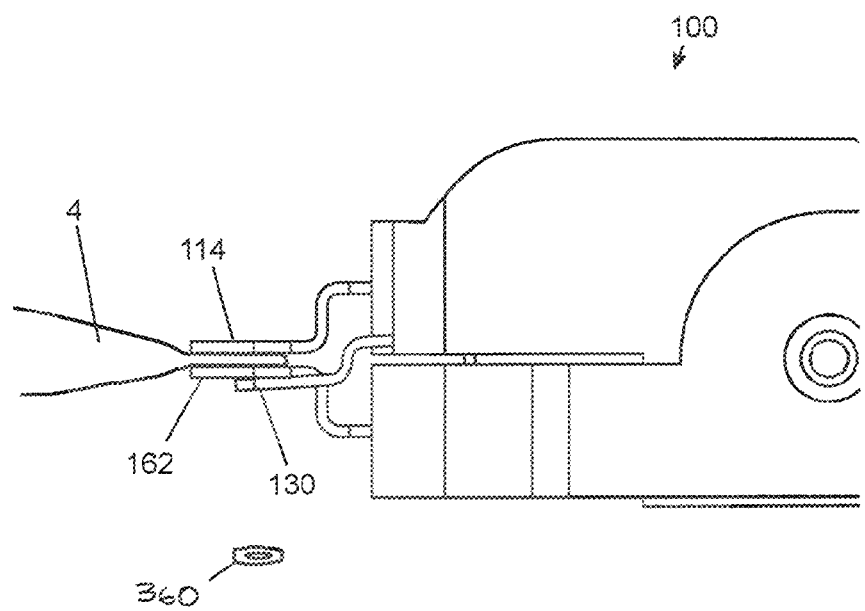
FIG. 27 is an expanded side elevational view of the distal portion of the objects of FIG. 26.
Figure 28:
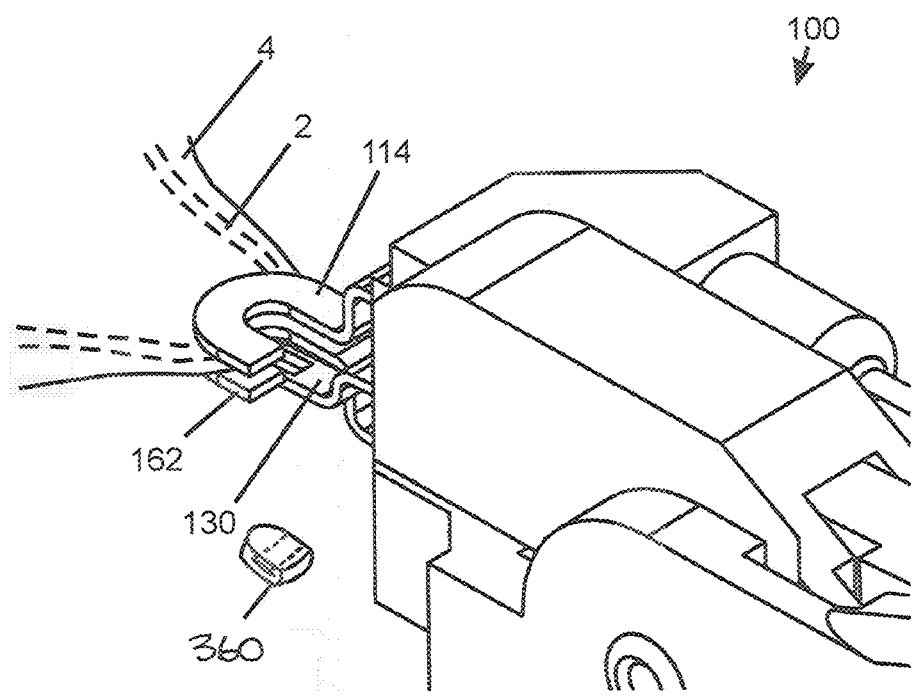
FIG. 28 is an expanded perspective view of the objects of FIG. 27.

A vasectomy procedure performed according to the method of this invention using instruments 100 and 200 begins using the same initial steps as a conventional vasectomy. That is, a vas duct is located and trapped within a fold of scrotal skin as shown in FIG. 1, and is retained in the fold using a clamp as shown in FIG. 2, except clamp 200 is used as shown in FIGS. 18 and 19 in which vas duct 2 is retained in a fold of scrotal skin 4 by clamping surfaces 214. (FIGS. 16 and 17) Arched portions 216 provide clearance for the fold and duct 2. Subsequently, as shown in FIGS. 20 through 23, the fold of scrotal skin 4 and vas duct 2 are positioned between lower jaw 162 and upper jaw 114 of instrument 100 and clamped by the jaws, the clamping pressure being maintained by the ratchet assembly formed by arm 176 and proximal portion 108 of member 104 (FIG. 12). Gap 236 (FIG. 13) between distal arcuate portions 224 of jaws 114 and 162 and members 104 and 152 of device 100 allow distal end 312 of clamp 300 to be positioned such that jaws 114 and 162 can be closed on tissue placed between them without interference from distal portion 312 of clamp 300. When the jaws are clamped as shown in FIGS. 22 and 23, RF energy from the electrosurgical generator is supplied to jaws 114 and 162 causing thermal coagulation of the scrotal skin 4 and the portion of vas duct 2 between jaws 114 and 162 so as to fuse the tissue into a contiguous mass. When coagulation of the tissue is complete, clamp 300 is removed. The coagulated tissue remains clamped between jaws 114 and 162 as shown in FIGS. 24 and 25. Tissue in the central region 238 of jaws 114 and 162 is not coagulated. The electrosurgical generator is activated again and member 120 is rotated causing electrode 130 to advance to a position below lower jaw 162 so as to electrosurgically remove the uncoagulated tissue 360 in the central region 238 of jaws 114 and 162. The generator is then deactivated, member 120 is released allowing electrode 130 to return to its first position. Portion 186 of ratchet arm 176 is depressed releasing teeth 192 from tapered distal facing portion 110 of portion 108 of member 104 releasing the clamping force between jaws 114 and 162. Instrument 100 is now ready to perform the same procedure on the other vas deferens.

Figure 29:
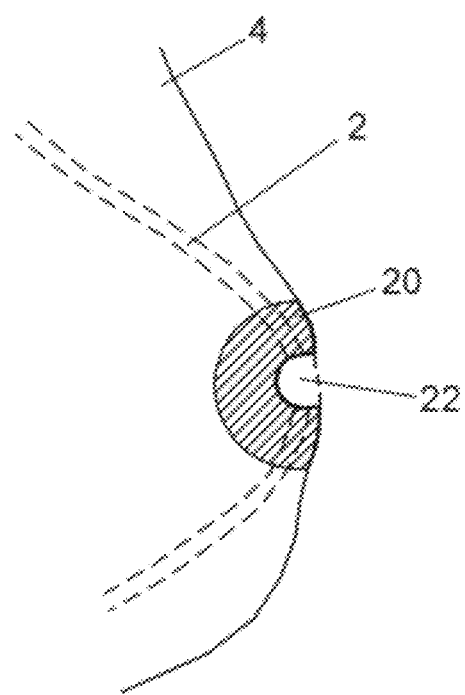
FIG. 29 depicts the site after completion of a vasectomy procedure in accordance with the principles of this invention.
Figure 30:
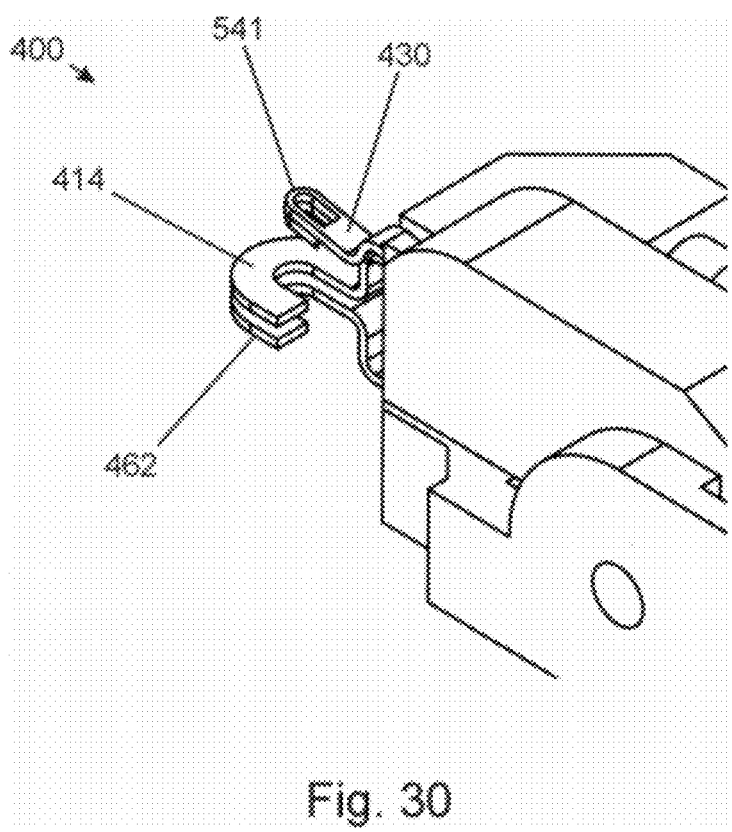
FIG. 30 is an expanded perspective view of the distal portion of an alternate embodiment formed in accordance with the principles of this invention.
Figure 31:
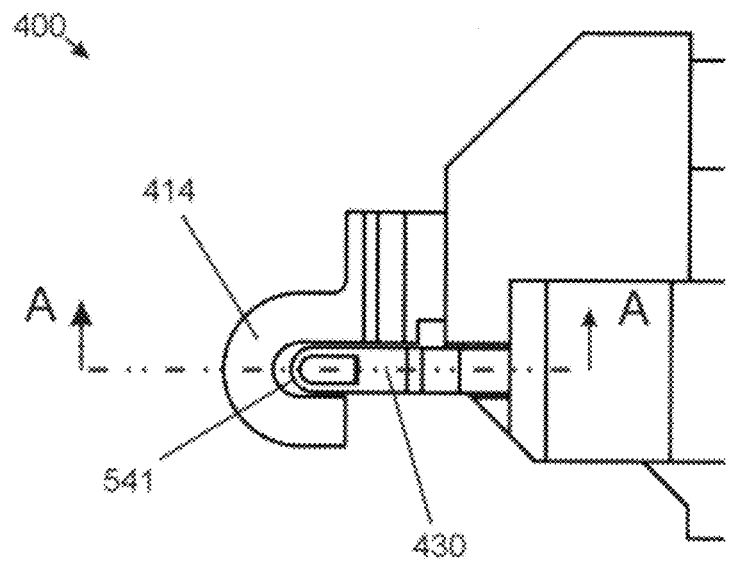
FIG. 31 is a plan view of the objects of FIG. 30.
Figure 32:
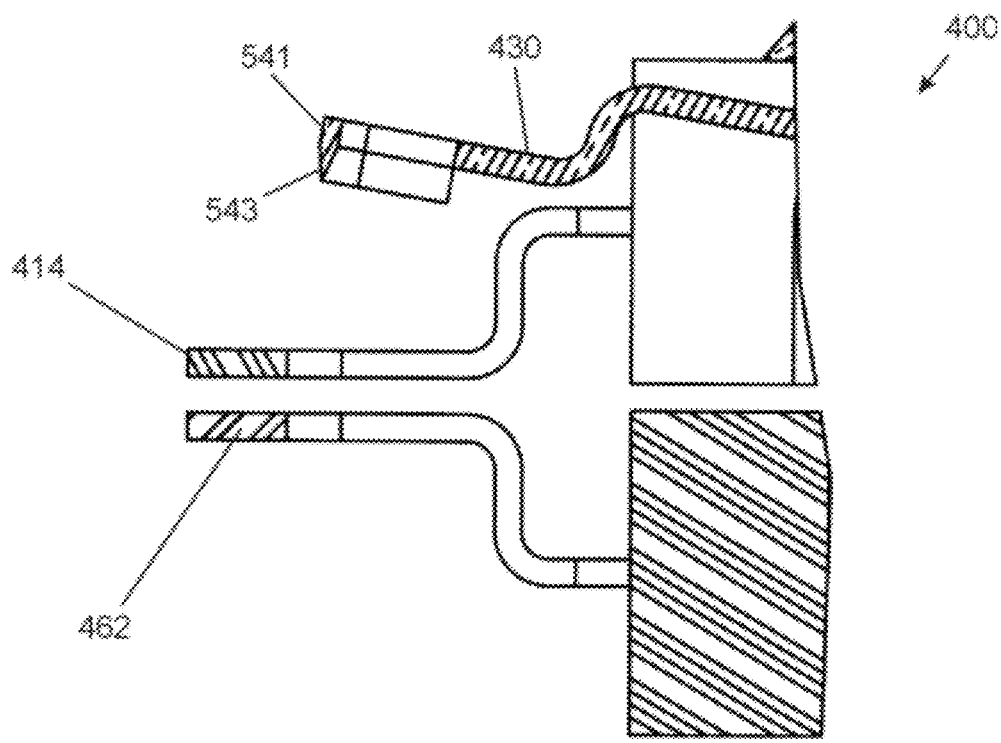
FIG. 32 is an expanded side elevational sectional view of the objects of FIG. 30 at location A-A of FIG. 30.

One skilled in the art will readily recognize that numerous changes may be made to instrument 100 without departing from the principles of this invention. For instance, resection of tissue portion 360 from center portion 129 of jaws 114 and 162 is accomplished by electrode 150. In other embodiments tissue portion 360 is resected by a conventional (non-electrosurgical) cutting feature. FIGS. 30 through 32 depict the distal portion of an embodiment in which center tissue portion 360 is removed by a sharpened edge not connected to the electrosurgical generator. Instrument 400 is identical to instrument 100 in all aspects except that electrode 130 of device 100 is replaced by cutting element 430. Element 430 (not connected to generator 50) has at its distal end perimetral ring 541 which has a sharpened lower portion 543 forming a cutting edge. When coagulation of arcuate portion 20 (FIG. 29) is completed by clamping jaws 414 and 462 and clamp 300 has been removed, tissue portion 360 is removed by cutting edge 543. In another embodiment, the distal portion of which is depicted in FIGS. 33 through 35, tissue portion 360 is resected from the center of the arcuate coagulated tissue portion by a cutting edge integral with one of the clamping jaws. A cutting element, either electrosurgical like element 130 of instrument 100, or conventional like element 430 of instrument 400, is not required thereby allowing the construction of the instrument to be simplified. Distal end 660 of member 652 has an added distal portion 663 which supports lower jaw 662 and has a portion 665 positioned beneath cutting edge portion 615 of upper jaw 614. Cooperative interaction between cutting edge 615 of upper jaw 614 and portion 665 of portion 663 cuts tissue placed therebetween, separation of the tissue occurring when jaws 614 and 662 are clamped together. Device 600 is advantageous since removal of tissue portion 360 is accomplished with clamp 300 in place so as to ensure that a portion of vas deferens 2 is removed. In another embodiment, the cutting element (element 130 of device 100, or element 430 of device 400) is configured such that tissue portion 360 can be removed by the element without removal of clamp 300.

In yet another embodiment, removal of tissue portion 360 is accomplished by a second instrument, either a conventional cutting device such as, for instance a scalpel, or by an electrosurgical instrument such as, for instance, a standard Bovie knife.

Generator 50, when operated in bipolar mode, is activated using a foot-pedal, RF energy being supplied to devices electrically connected to the bipolar output while the foot-pedal is depressed. The time required to achieve a desired clinical effect is determined by the clinician operator. When using instrument 100, the time required for coagulation is determined by the operator who determines the length of time that his foot depresses the foot-pedal. In a preferred embodiment instrument 100 is part of a system in which generator 50 is a low-cost dedicated generator designed for use only with instrument 100. Specialized generator 50 of this embodiment is low-cost since it has only one output, a bipolar one, at a fixed power level using a single waveform. Dedicated generator 50 has other advantages, primarily with regard to the coagulating portion of the process. In a preferred embodiment generator 50 has a means for determining the time duration during which RF power is applied to the tissue for coagulation. In a preferred embodiment, the impedance of the tissue between the jaws is monitored. Because the impedance of tissue changes during coagulation, RF power may be applied until a predetermined impedance value is reached, or until a predetermined degree of impedance change is reached. In another embodiment the means is a timer which may be set by the operator or which is preset.

INDUSTRIAL APPLICABILITY

As noted previously herein, the vasectomy device, kit and method for performing vasectomies of the present invention overcome disadvantages and deficiencies of conventional vasectomy materials and methods by providing a rapid, reliable, less invasive male sterilization procedure that reduces or eliminates negative side effects, including swelling and spontaneous regeneration, and minimizes recovery time and recovery restrictions. It further minimizes the potential for exposure to patient bodily fluids, thereby minimizing the potential for transmission of blood-borne diseases such as HIV and Hepatitis. For example, the vasectomy method herein described does not produce bleeding and, aside from the needle used for injection of the local anesthetic, does not require the use of any sharp instruments which could inadvertently penetrate the skin of the operator. Thus, the procedure may be performed on patients who are, for instance, HIV positive, with minimal risk to the clinician compared to other methods.

Because of the complications associated with traditional vasectomies but eliminated by the technique and device herein disclosed, successful procedures have, in the past, required the utilization of skilled experienced surgeons. The vasectomy device and method of the instant invention minimizes the number of steps and duration of the procedure, thereby allowing the procedure to be quickly completed by clinicians with minimal training Moreover, given its simplicity, less skilled heath care workers can master the procedure in relatively short period of time. This will extend the feasibility of male sterilization to areas of the world where doctors, more particularly skilled surgeons, are in short supply. For example, the instruments, kit and method of the instant invention may be advantageously used for population control in developing countries. In such countries, the availability of an electrosurgical generator, or even of suitable means for powering an electrosurgical generator may be limited. In such environments, it may be desirable to utilize a dedicated special-purpose generator 50 includes a rechargeable power source. In yet another embodiment, generator 50 with the rechargeable power source mounts to instrument 100 such that instrument 100 and generator 50 together form an assembly.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed:

1. A method for performing a vasectomy comprising the steps of:
   (a) locating a vas deferens within a scrotum;
   (b) temporarily isolating a length of the vas deferens in a fold of scrotal skin;
   (c) placing upper and lower clamping jaws of a vasectomy device around a portion of the isolated scrotal skin containing the length of vas deferens and clamping said upper and lower clamping jaws together such that said upper and lower jaws retain an arcuate area of clamped scrotal tissue containing a first and second segment of the vas deferens and further comprise an interior perimeter which defines a convex area of unclamped scrotal tissue that contains a third segment of the vas deferens;
   (d) excising some or all of the convex area of unclamped scrotal tissue, including said third segment of the vas deferens, and sealing the arcuate area of clamped scrotal tissue including said first and second segment of the vas deferens; and
   (e) removing said upper and lower clamping jaws from the isolated scrotal skin immediately after step (d).

2. The method of claim 1, wherein the locating step is accomplished by digital manipulation.

3. The method of claim 1, wherein the isolating step is accomplished by means of a vas clamp.

4. The method of claim 1, wherein said vasectomy device comprises a proximal portion that comprises a handle and a distal portion that comprises said upper and lower clamping jaws, further wherein said upper and lower clamping jaws are opposingly faced, arcuate, and engage to define an interior perimeter comprised of a continuous curve.

5. The method of claim 4, wherein said upper and lower arcuate jaws are "U" shaped.

6. The method of claim 1, wherein the clamping of step (c) results in physical crushing of the arcuate area of clamped scrotal tissue.

7. The method of claim 1, wherein said excising step includes the steps of cutting along a path defined by the interior perimeter of said arcuate area of clamped scrotal tissue.

8. The method of claim 1, wherein said sealing is achieved by means of surgical adhesive, suture, cauterization or a combination thereof.

9. The method of claim 8, wherein said cauterization is accomplished by means of a bipolar cauterizing flow.

10. The method of claim 1, said clamping step further comprises the steps of:
   a. connecting said vasectomy device to a power source; and
   b. applying power to the arcuate area of clamped scrotal tissue so as to thermally coagulate the first and second segment of the vas deferens contained therein.

11. The method of claim 10, wherein said power source comprises a radio frequency (RF) generator.

* * * * *